United States Patent
Rastashanskiy et al.

(10) Patent No.: US 10,456,373 B2
(45) Date of Patent: Oct. 29, 2019

(54) AGENT EXHIBITING ANTI-STRESS, ANXIOLYTIC AND ANTI-DEPRESSION ACTIVITY, AND COMPOSITION BASED THEREON

(71) Applicant: OBSHCHESTVO S OGRANICHENNOY OTVETSTVENNOSTYU "NORMOFARM", Abaza Respublike Khakasiya (RU)

(72) Inventors: Viacheslav Valerievich Rastashanskiy, Moscow (RU); Konstantin Sergeevich Ostrenko, Obninsk (RU)

(73) Assignee: OBSHCHESTVO S OGRANICHENNOY OTVETSTVENNOSTYU "NORMOFARM", Abaza Respublika Khakasiya (RU)

( * ) Notice: Subject to any disclaimer, the term of this patent is extended or adjusted under 35 U.S.C. 154(b) by 0 days.

(21) Appl. No.: 15/950,194

(22) Filed: Apr. 11, 2018

(65) Prior Publication Data

US 2018/0228766 A1    Aug. 16, 2018

Related U.S. Application Data

(63) Continuation of application No. PCT/RU2016/050049, filed on Oct. 10, 2016.

(30) Foreign Application Priority Data

Oct. 23, 2015 (RU) ................................ 2015145777

(51) Int. Cl.
| | |
|---|---|
| *A61K 31/375* | (2006.01) |
| *A61K 31/4415* | (2006.01) |
| *A61K 31/51* | (2006.01) |
| *A61P 25/22* | (2006.01) |
| *A61P 25/24* | (2006.01) |
| *A61P 25/00* | (2006.01) |
| *A61K 45/06* | (2006.01) |

(52) U.S. Cl.
CPC ........ *A61K 31/375* (2013.01); *A61K 31/4415* (2013.01); *A61K 31/51* (2013.01); *A61K 45/06* (2013.01); *A61P 25/00* (2018.01); *A61P 25/22* (2018.01); *A61P 25/24* (2018.01)

(58) Field of Classification Search
CPC ..................................................... A61K 31/375
USPC ............................................................ 514/474
See application file for complete search history.

(56) References Cited

FOREIGN PATENT DOCUMENTS

| | | |
|---|---|---|
| CN | 103896891 A | 7/2014 |
| RU | 2322240 C1 | 4/2008 |
| RU | 2351326 C2 | 4/2009 |
| RU | 2367427 C1 | 9/2009 |
| RU | 2428992 C1 | 9/2011 |
| RU | 2444358 C1 | 3/2012 |
| RU | 2477722 C1 | 3/2013 |
| RU | 2505294 C1 | 1/2014 |
| WO | WO 200003701 A1 | 1/2000 |

OTHER PUBLICATIONS

Haddjeri N, et al. Increased tonic activation of rat forebrain 5-HT(1A) receptors by lithium addition to antidepressant treatments. Neuropsychopharmacol 2000; 22(4):346-356.
Moretti M, et al. Protective effects of ascorbic acid on behavior and oxidative status of restraint-stressed mice. J Mol Neurosci. 2013;49(1):68-79.
Binfare RW, et al. Ascorbic acid administration produces an antidepressant-like effect: evidence for the involv. Prog Neuropsychopharmacol Biol Psychiatry. 2009;33(3):530-40.
Normotim—stress-resistance// newspaper "Na zdorovje", No. 10, Oct. 2015, published on May 10, 2015. http://medgazeta-tomsk.ru. Registration certificate RU.77.99.11.003.E.005286.02.11 Biologically active food supplement "Normotim".

*Primary Examiner* — Kevin E Weddington
(74) *Attorney, Agent, or Firm* — Dmitry S. Kryndushkin

(57) ABSTRACT

The agent with antistress, anxiolytic and antidepressant activity and a composition based on it. The invention relates to the field of pharmaceutics, particularly to chemical compounds based on lithium salts, namely to substances with antistress, anxiolytic and antidepressant activity and can be used in medicine, veterinary medicine, and the pharmaceutical industry. The invention discovers the possibility of using lithium ascorbate as an agent with antistress, anxiolytic and antidepressant activity. The claimed composition with antistress, anxiolytic and antidepressant activity, including a lithium salt, contains pyridoxine hydrochloride, thiamine mononitrate and lithium ascorbate as a lithium salt. The use of lithium ascorbate as an agent with antistress, anxiolytic and antidepressant action and the composition based on it, enables to expand the assortment of the agents for indicated administration. At the same time, the claimed agents have low toxicity and high efficacy.

3 Claims, No Drawings

AGENT EXHIBITING ANTI-STRESS, ANXIOLYTIC AND ANTI-DEPRESSION ACTIVITY, AND COMPOSITION BASED THEREON

FIELD CROSS-REFERENCE TO RELATED APPLICATIONS

The present application is a continuation of PCT/RU2016/050049 filed on Oct. 10, 2016. This application also claims the benefit of Russian Patent Application RU 2015145777 filed on Oct. 23, 2015. The contents of the abovementioned applications are incorporated by reference herein.

FIELD OF INVENTION

The present invention relates to the field of pharmaceuticals, specifically, to chemical compounds based on lithium salts, namely to the substances with antistress, anxiolytic, and antidepressive activity, and can be used in medicine, veterinary science, or pharmaceutical industry.

The claimed agent is proposed to be used for production of complex preparations on its basis, and also as a constituent element in various medicinal and pharmaceutical forms: balsams, solutions, and tablets.

BACKGROUND

Lithium ascorbate is known to be used as a constituent element in the composition exhibiting antioxidant and immunostimulating activity (RU No 2444358 C1, 10 Jan. 2012), as an agent for increasing neutrophil efficiency (RU 15 No 2226391 C2, 10 Jan. 2004), as a hematoprotective agent (RU No 22351326 10 Apr. 2009).

All the mentioned references about lithium ascorbate do not disclose or suggest its potential antidepressive, anxiolytic, and antistress properties. Analysis of the available prior art showed that no data on antidepressive, anxiolytic, or antistress activities of lithium ascorbate have been previously published by others.

There are currently in use lithium salt-based compositions with nootropic activity. There is currently in use a lithium salt n-(4-acetoxybenzoyl) glycine (RU 2505294, 27 Jan. 2014), which refers to new water-soluble lithium salts of glycine derivative (aminoacetic acid) with 4-hydroxybenzoic acid. The said agent enables to obtain a highly effective water-soluble glycine derivative and 4-hydroxybenzoic acid combining the main effects inherent to tranquilizing and nootropic agents.

From the data source (RU 2322240 C1, 20 Apr. 2008), there is a pharmaceutical composition possessing nootropic activity and comprising an active substance dimephosphon. The pharmaceutical in the form of aqueous solution contains additionally citric acid and lithium carbonate with the following ratio of the components, mass %: dimephosphon 15.0-30.0; lithium carbonate 0.5-5.0; citric acid 3.0-4.0; deionized water—up to 100. A shortcoming of the said composition is its considerable toxicity due to the usage of the lithium salt (lithium carbonate) possessing high toxicity.

There also exists a preparation (known from patent RU 2428992 C1, 20 Sep. 2011) for correcting stress conditions in livestock comprising lithium oxybate, sodium selenite, ascorbic acid and water for injections in the ratio of the components (in mass %): lithium oxybate—4.0-7.0; sodium selenite—0.2-0.5; ascorbic acid—3.0-12.0; water for injections—the rest. The preparation possesses a marked nootropic activity and immunostimulating action, and is convenient for administration. A shortcoming of the said composition is usage of lithium oxybate having a variety of side effects such as general malaise, dizziness, drowsiness, muscle weakness, tremor of the upper extremities, sinus tachycardia, dyspeptic events, diarrhea, tremor, tic, development of diffuse nontoxic goiter, allergic reactions.

A lithium salt of comenic acid and usage thereof as antioxidant and stress- and neuroprotective agent is known from the patent (RU 2477722 C1, 20 Mar. 2013). It follows from the said patent that (RU 2477722 C1, 20 Mar. 2013) that a lithium salt of comenic acid is obtained by mixing a comenic acid solution, heated to the temperature of 80±2° C., with the stoichiometric amount of the solution of carbonate or lithium hydroxide and coloring the solution in yellow and a pH value of the solution of 4.6 or 10.0, respectively, and isolating the lithium salt of comenic acid from the solution by distilling off the water under vacuum. A lithium salt of comenic acid belongs to the agents for the prevention and treatment of neurodegenerative diseases caused by oxidative damage of the brain. For this purpose, a lithium salt of lithium comenic acid is proposed to be taken in the amount of 2 mg per 1 kg of body weight once daily for 3 days. A disadvantage of this invention is that it is aimed only at the prevention and treatment of neurodegenerative diseases caused by oxidative brain damage.

There is a lithium-containing agent for the prevention and treatment of cerebrovascular diseases (RU 2367427 C1, 20 Sep. 2009). The mentioned agent for the treatment and prevention of cerebrovascular diseases contains a lithium salt where the lithium cation is bound to the anion of an organic acid from a group of the following: adipate, aspartate, benzoate, gamma linolenoate, glycinate, gluconate, nicotinate, orotate, salicylate, citrate. The lithium-containing agent for the prevention and treatment of cerebrovascular diseases ensures the efficiency of treatment at low doses of the indicated agent. However, this agent is aimed only at the prevention and treatment of stroke.

The closest to the claimed composition is an agent containing lithium carbonate used as a medicine by patients in a manic phase and for the prevention of exacerbation of bipolar affective disorders, schizoaffective disorders, manic conditions of various genesis, affective disorders in chronic alcoholism, drug dependence, sexual abnormalities, Meniere's syndrome, migraine [M. D. Mashkovsky, Lekarstvenniye Sredstva: Posobiye dlya vrachei.-T.1.-Moscow: Novaya Volna.-2002.-p. 109-110]. The main shortcoming of this agent is low bioavailability that results in the need for high dosages, as well as high toxicity (LD50=531 mg/kg), which leads to numerous side effects: tremor, drowsiness, adynamia, cardiac rhythm disturbance, myasthenia gravis, increased thirst, polyuria and renal dysfunction. This considerably narrows the therapeutic range, with a high risk of overdose.

SUMMARY OF THE INVENTION

The claimed group of inventions is aimed at broadening the arsenal of drug candidates with anti-stress, anxiolytic and antidepressant actions. The technical result achieved in the current invention is the fact that the claimed agents and compositions possess antistress, anxiolytic and antidepressant properties. Further, the claimed agent (lithium ascorbate) and the corresponding compositions based on the agent have an increased efficacy at low doses and low toxicity in comparison with the known drugs.

Lithium ascorbate as an agent with antistress, anxiolytic and antidepressant effect is proposed to solve this problem. In some embodiments, the compositions based on current invention may also contain additional active ingredients beneficial for subjects suffering from stress. Such additional ingredients may further increase beneficial effect of lithium ascorbate. Some of the additional ingredients that can be used in combination with lithium ascorbate include Vitamin A, Vitamin D, Vitamin E, Vitamin K, Vitamin B1, Vitamin B2, Niacin, Pantothenic acid, Vitamin B6, Folic acid, Vitamin B12, Biotin, Vitamin C, Calcium, Magnesium, Iron, Copper Iodine, Zinc, Manganese, Sodium, Potassium, Selenium, Chromium, Molybdenum, Fluoride, Chloride, Phosphorus, Levocarnitine, Pantothenic acid (vitamin B5), Choline (vitamin B4), Folic acid (vitamin B9), Glycin (Gly, G), Leucine (Leu, L), Tyrosine (Tyr, Y), Serine (Ser, S), Glutamic acid (Glu, E), Glutamine (Gln, Q), Asparagic acid (Asp, D), Asparagine (Asn, N), Phenylalanine (Phe, F), Alanine (Ala, A), Lysine (Lys, K), Arginine (Arg, R), Histidine (His, H), Cysteine (Cys, C), Valine (Val, V), Proline (Pro, P), Hydroxyprolin (Hyp, hP), Tryptophan (Trp, W), Isoleucine (Ile, I), Methionine (Met, M), Treonine (Thr, T), Hydroxylysine (Hyl, hK), β-Alanine, PQQ (vitamin B14), Astaxanthin, Coenzyme Q10, Succinic acid, Hydroxy-butanedioic acid, Meldonium, Indole-3-carbinol, Rutin.

In preferred embodiments, the compositions based on current invention contain vitamin B1 (in the form of thiamine mononitrate) and vitamin B6 (in the form of pyridoxine hydrochloride) in combination with lithium ascorbate. In such embodiments alternative forms of vitamin B1 and vitamin B6 may also be used (such as thiamin hydrochloride or pyridoxine 5'-phosphate).

In some embodiments, a method of treating a subject suffering from stress, anxiety and depression, comprising administering to the subject an effective amount of a composition comprising lithium ascorbate, whereby the administration of the composition treats stress, anxiety or depression in the subject, is claimed. In preferred embodiments, the effective amount of the composition in the indicated method is determined by the the following dosage of lithium ascorbate: 0.06-20 mg lithium ascorbate per 1 kg of the subject body mass daily. The preferred composition may further comprise vitamin B6 and vitamin B1. In the other embodiments, the compositions can be combined or mixed with a pharmaceutically active agent, a carrier, and/or an excipient. Examples of such components are described herein. The combined compositions can be formed into a unit dosage as tablets, capsules, gel capsules, slow release tablets, or the like. In preferred embodiments, the following mass ratio (%) of lithium ascorbate, pyridoxine hydrochloride, thiamine mononitrate is preferred to be used in the compositions: Lithium ascorbate: 10-90%; Pyridoxine hydrochloride: 6-50%; Thiamine mononitrate: 4-40%.

The claimed agent and compositions on its basis may broaden the range of drug candidates that can be used to increase stress resistance, reduce anxiety, emotional disturbance, and also act as antidepressants. Furthermore, lithium ascorbate has an anti-stress, anxiolytic and antidepressant effect, and thiamine mononitrate and pyridoxine hydrochloride also have a beneficial effect on the central and peripheral nervous systems. Thiamine optimizes cognitive activity and brain function. Pyridoxine hydrochloride plays an important role in the metabolism and is involved in the synthesis of neurotransmitters. Taken together, it results in a synergic effect by enhancing the anti-stress, anxiolytic and antidepressant effect of the composition, and leads to high efficacy of the claimed composition based on lithium ascorbate administered in small doses.

As shown below, the claimed substance ranges of the compositions in one of the preferable implementation variants of lithium ascorbate-based composition provide anti-stress, anxiolytic and antidepressant activity at various ratios of the components in the claimed ranges. However, these ranges of components in the claimed compositions are not strictly essential, since with the pharmaceutically acceptable component compositions of lithium ascorbate, pyridoxine hydrochloride and thiamine mononitrate, the claimed agent and composition will be sufficiently effective for antistress, anxiolytic and antidepressant activity.

DETAILED DESCRIPTION OF THE INVENTION

The anti-stress, anxiolytic and antidepressant effects of the claimed agent and compositions on its basis were determined as follows. To confirm a potential application of lithium ascorbate as an agent with anti-stress, anxiolytic and antidepressant effect, standard stress tests were carried out on white Wistar rats, a common breed that has been commonly used for preclinical studies of new drug candidates:

1. The suspension test. Five animals from each group were used. Each animal was suspended for 24 hours. After that the sample of whole blood was taken from the sublingual vessels of that animal. Then the animal was placed in a desiccator with diethyl ether. 60 minutes later a spinal decapitation of the animal was performed. The abdominal opening was performed and the number of ulcers on the inner surface of the stomach was counted. The obtained whole blood was placed in two test tubes. The whole blood was used to determine the number of eosinophils by the Duncker method. Serum was used to determine the biochemical composition of the blood. Adrenaline and norepinephrine were determined as biochemical indices. These characteristics are specific markers identifying the impact of stress factors of various etiologies.

2. The transport stress simulation test. Five animals from each group were used. The animals were placed in cages fixed on a laboratory shutter. The duration of the test was 240 minutes. At the end of the test the animals were examined by the techniques described in paragraph 1. A sample of whole blood was taken to determine the number of eosinophils by the Duncker method. The blood serum was studied to measure the amount of enzymes: alanine aminotransferase (ALT), aspartate aminotransferase (AST), creatinine.

The tests were carried out on 2-month-old rats of the Wistar line. The groups were selected according to the principle of paired counterparts. For this purpose, six groups of animals of 30 animals each were formed: group #1— control (rats receive water); group #2— experimental, lithium ascorbate dosage of 120 mg/kg of animal body weight; group #3— experimental, lithium ascorbate dosage of 60 mg/kg of animal body weight; group #4—experimental, lithium ascorbate dosage of 30 mg/kg of animal body weight; group #5—intact rats (not envoloved in the tests, naturally developing under the same conditions of keeping in the vivarium); group #6—experimental, lithium ascorbate dosage of 60 mg/kg of the animal body weight, administered in pills (the pills had total mass of 0.2-0.25 g, and cocoa butter was used as an excipient).

During the course of the study the animals were selected from the formed groups of 10 animals each to participate in stress tests, 5 animals per test. The selection was made on the 7th, 14th, 21st day of the drug administration (experiments were performed on the same days right after selection). The animals were weighed weekly immediately before testing. The obtained data were processed by statistical methods of mathematical statistics. The drug was administered to the animals of the 2nd, 3rd and 4th groups in solution through a gastric tube. Water for injection produced by the "Bufus Novosibkhimpharm" was used as a solvent. The introduced volume was 1.5 ml. The solution was introduced at the same time 2 hours after morning feeding. The first group was given water for injection by the same way. The volume of administration was 1.5 ml.

The efficacy and safety of lithium ascorbate as an antistress, anxiolytic and antidepressant agent can be supported by the following examples. While preferred embodiments of the present invention have been shown and described herein in the following examples, it will be obvious to skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Example 1. Method of Studying Antistress and Anxiolytic Activity—a Suspension Test During the test a change in the reaction of the animals was observed during prolonged administration of the preparation. Three sequences of the experiment were performed with a periodicity of 7 days. The drug was administered from the first day of the study daily without a break. Thus, accumulation of the drug in the animal body occurred. Five animals from each group were used in each sequence of the experiment (the animals were suspended for 24 hours). After this, blood samples were taken from the sublingual vessels. Further, the animal was euthanized with diethyl ether. Decapitation and dissection of the abdominal cavity were performed to calculate the number of ulcers on the inner surface of the stomach. The rats as objects for the study of psychotropic drugs are a successful model. They react quickly to various stress factors. It is convenient to evaluate the efficacy of drugs due to various factors beginning with physiological, behavioral, biochemical and other parameters. In the suspension test, it is possible to determine the overall psycho-emotional state of the animal in addition to physical endurance.

A suspension test enables to determine the ability of the body to adapt quickly to long-term adverse impact, evaluate physical endurance, study behavioral state and evaluate adaptation ability (by showing psychostimulant activity). During the study lithium ascorbate was found to increase physical endurance. The experimental animals, compared to the control ones, under equally unfavorable conditions, tried to adapt to them more quickly and more efficiently. The animals on lithium ascorbate tried to reach the attachment point (in the withers area) with their front limbs and fix their position of the body with their forelegs. Some animals tried to free themselves by making translational movements. Thus, the animals showed an anti-stress and anxiolytic effect of lithium ascorbate, which reduced the impact of the stress factor. The control animals, on the contrary, in the first stage wriggled all over the body, haphazardly waved their limbs and when reached a point of exhaustion, hang without any movements. The number of defecation acts from the control animals was 3-4 times more than from the animals treated with lithium ascorbate compositions.

The physiological, morphological and biochemical characteristics, such as the determination of ulcers in the stomach, eosinophils in whole blood, epinephrine and norepinephrine in blood serum were estimated as main and most informative indicators of the onset of a stress state in a living organism and of overall impact on the body. A part of the whole blood sample was used to count eosinophils by Duncker test. The other part of the blood sample was used to produce serum to determine adrenaline and norepinephrine. The data are shown in Tables 1, 2, 3.

TABLE 1

Number of identified ulcers in the stomach in the test on physical endurance (the suspension test)

| Group No. | Number of ulcers in the stomach | | |
|---|---|---|---|
| | Administration day 7 | Administration day 14 | Administration day 21 |
| 1 | 23.5 ± 0.9 | 21.2 ± 0.2 | 21.2 ± 0.2* |
| 2 | 4.0 ± 0.5* | 2.5 ± 1.1* | 2.1 ± 0.7 |
| 3 | 4.1 ± 0.8 | 2.6 ± 0.4 | 2.4 ± 0.5 |
| 4 | 4.5 ± 0.9 | 2.4 ± 0.2* | 1.9 ± 0.4 |
| 5 | 1.0 ± 0.1 | 1.5 ± 0.5 | 1.0 ± 0.5 |
| 6 | 8.7 ± 1.2 | 1.6 ± 0.9 | 1.5 ± 0.6* |

(*$p < 0.05$ when compared by t-test with the control group 1)

1—the control group;

2—120 mg/kg ascorbate lithium;

3—60 mg/kg ascorbate lithium;

4—30 mg/kg ascorbate lithium;

5—the intact group;

6—60 mg/kg in the form of pills with cocoa.

TABLE 2

Determination of the eosinophil count in whole blood by Duncker (the suspension test)

| Group No. | Eosinophil count in whole blood | | |
|---|---|---|---|
| | Administration day 7 | Administration day 14 | Administration day 21 |
| 1 | 311.6 ± 5.8 | 285 ± 1.5 | 291 ± 0.2 |
| 2 | 768 ± 6.7 | 885 ± 3.8 | 911 ± 8.2 |
| 3 | 791 ± 1.2* | 866 ± 9.4 | 910 ± 4.1* |
| 4 | 764 ± 6.5 | 897 ± 7.2 | 954 ± 9.7 |
| 5 | 953 ± 2.9 | 975 ± 0.5 | 981 ± 5.4 |
| 6 | 653 ± 9.2 | 913 ± 0.9* | 954 ± 3.6 |

(*$p < 0.05$ when compared by t-test with the control group 1)

1—the control group;

2—120 mg/kg ascorbate lithium;

3—60 mg/kg ascorbate lithium;

4—30 mg/kg ascorbate lithium;

5—the intact group;

6—60 mg/kg in the form of pills with cocoa.

TABLE 3

Determination of adrenaline and noradrenaline level in blood serum
(the suspension test)

Adrenaline and noradrenaline level in blood serum

| Group # | Administration day 7 | | Administration day 14 | | Administration day 21 | |
|---|---|---|---|---|---|---|
| | Adrenaline µg/l | Noradrenaline µg/l | Adrenaline µg/l | Noradrenaline µg/l | Adrenaline µg/l | Noradrenaline µg/l |
| 1 | 27.1 ± 3.91 | 68.6 ± 1.52 | 28.3 ± 1.27 | 68.9 ± 9.41 | 27.7 ± 2.46 | 70.5 ± 3.54 |
| 2 | 7.6 ± 0.38 | 20.2 ± 5.67 | 8.7 ± 3.82 | 20.3 ± 4.83 | 9.6 ± 3.28 | 18.4 ± 5.27 |
| 3 | 7.9 ± 0.21* | 22.1 ± 1.98 | 7.1 ± 1.19 | 20.3 ± 3.49 | 7.3 ± 2.14* | 19.3 ± 6.13 |
| 4 | 8.1 ± 0.52 | 24.3 ± 2.2 | 6.9 ± 2.77 | 18.2 ± 5.28 | 6.9 ± 0.97* | 17.9 ± 0.95* |
| 5 | 6.7 ± 0.65 | 18.6 ± 1.95 | 6.1 ± 0.51 | 17.9 ± 0.85 | 6.4 ± 2.42 | 17.2 ± 0.56 |
| 6 | 22.6 ± 4.27 | 54.8 ± 10.4 | 6.7 ± 0.96* | 18.4 ± 0.49 | 7.9 ± 3.61 | 17.8 ± 0.98* |

(*$p < 0.05$ when compared by t-test with the control group 1)
1—the control group;
2—120 mg/kg ascorbate lithium;
3—60 mg/kg ascorbate lithium;
4—30 mg/kg ascorbate lithium;
5—the intact group;
6—60 mg/kg in the form of pills with cocoa.

Based on the aggregate data obtained from testing the anti-stress efficacy of lithium ascorbate, it can be concluded that oral administration of aqueous solutions of lithium ascorbate leads veridically to rapid adaptation of the body to stress. The first test performed 7 days later gave slightly higher results than those in the intact group (group #5), but the second test (14 days after the start of the experiment) data were close to the intact group, the results being obtained at almost all dosages. It should also be noted that all measured characteristics in all the tests were 2.5-3.5 times and in the case of ulcer count were more than 10 times higher than those of the control group (group #1). A decrease in the level of hormones of fear—adrenaline and norepinephrine—3,5-4 times indicates an expressed anxiolytic action of lithium ascorbate. The obtained data enables to draw an unambiguous conclusion about the high antistress and anxiolytic activity of lithium ascorbate.

Example 2. Transport Stress Simulation Test to Study Anti-Stress, Anxiolytic and Antidepressant Activity The rotating universal Shaker Unimax 10 was used as a model for simulating transport stress. The rotation speed was chosen at 120 rpm for 240 min A cage with five animals was fixed on the site. The rats stayed in the cage in a free state. A change in the reaction of animals with prolonged administration of the drug was observed. The sampling and decapitation process is described in Example 1.

Physiological, morphological and biochemical blood parametres were determined as markers of the impact of stress on animals, such as: individual and group behavior of animals, the number of enuresis acts, the number of defecation acts, and the number of excrement boluses; eosinophils in whole blood according to Duncker and the levels of ALT, AST enzymes and creatinine in the blood serum were measured.

Transport stress is a striking example of technological effect on animal and human body. During a short period of exposure, the animals did not have time to develop adaptive properties to compensate for that effect. Thus, it suits best as an indicator for the observation of the classical example of the development of the adaptive syndrome by Selye. In the experiment, a simulation of the transport impact on the rats was performed with the help of the laboratory shutter. Progressive 4 hour-long circular vibrations adversely affected the animals. The rats in the control group were constantly moving, colliding with each other trying to concentrate in the corners, where the amplitude of the oscillation was the highest. At the same time the number of defecation acts was higher. The animals behaved aggressively. The stronger ones tried to push out a weaker animal out of the corner. The data are given in Table 4.

The behavior of the animals in the experimental groups was different. There was a pronounced social interaction and the ability of animals to react more quickly to the exposure change. The animals tried to find a place with the slightest vibration. At the same time they gathered in groups, got up on their hind limbs and tried to move along with the platform. This behavior indicates that the animals lacked fear and anxiety. Trying to adapt to these conditions, animals moved less on the site, and grouped to reduce the negative impact. The numbers of enuresis and defecation acts were significantly less. Such behavior of animals, as well as the morphological parameters of whole blood, such as eosinophils, indicates a pronounced anxiolytic effect of lithium ascorbate. Eosinopenia is a characteristic of stressors of various etiology, as evidenced by the information from "Stress-induced disturbances in the blood system and their correction by mediators and metabolites of the stress-limiting systems," Ph.D. O. A. Makarova's topic of the dissertation and abstract for the VAC 14.00.16, 2003. The hematologic studies conducted after stress exposure showed that in the control group the number of eosinophils decreased more than 2 times compared to the intact animals. In the experimental groups the decrease was less marked and depended on the lithium ascorbate doses. The results of the study are given in Tables 4; 5; 6.

The antidepressant effect of lithium ascorbate was clearly observed based on the condition and behavior of the experimental and control animals. With prolonged shuttling the rats of the control group displayed complete indifference and apathy to what was happening around. After the experiment was stopped, the animals rested indifferently and did not demonstrate any actions aimed at its defense. The acts of defecation became disorderly, and the feces were not pronounced. The animals defecated and urinated at the same place where they lay and did not try to find a more convenient place. The rats treated with lithium ascorbate displayed motor activity after the experiment, despite the unstable position of their body. They tried to crouch in the cage to the drinking spout, while not showing aggression, but maintaining dominance. During attempts to take an animal away from the cage, it resisted and tried to hide. Thus, the instincts of hunger and self-preservation were not suppressed in the experimental groups.

Based on the studies conducted, it can be affirmed that lithium ascorbate is an anti-stress drug. The results obtained in this test confirm the conclusions made earlier in Example 1 on high antistress and anxiolytic activity of lithium ascorbate, and are supplemented with data allowing to establish the antidepressant effect of lithium ascorbate.

TABLE 4

Effect of different doses of lithium ascorbate on the number of boluses in defecation

| Group # | Administration day 7 Number of boluses | Administration day 14 Number of boluses | Administration day 21 Number of boluses |
|---|---|---|---|
| 1 | 8.6 ± 1.4 | 10.1 ± 2.7* | 11.6 ± 1.9 |
| 2 | 5.0 ± 1.1* | 4.1 ± 1.1 | 4.0 ± 1.0 |
| 3 | 4.6 ± 0.4 | 3.9 ± 0.4* | 3.7 ± 0.7 |
| 4 | 4.2 ± 0.4 | 3.9 ± 0.4* | 3.5 ± 0.3* |
| 5 | 3.6 ± 0.7 | 3.8 ± 0.4 | 3.5 ± 0.7 |
| 6 | 7.2 ± 1.5* | 5.2 ± 0.9 | 3.7 ± 0.3 |

(*$p < 0.05$ when compared by t-test with the control group 1)
1—the control group;
2—120 mg/kg ascorbate lithium;
3—60 mg/kg ascorbate lithium;
4—30 mg/kg ascorbate lithium;
5—the intact group;
6—60 mg/kg in the form of pills with cocoa.

Example 3. Ascorbate Efficacy in Small Doses

TABLE 5

Determination of the eosinophil count in whole blood by Duncker (the test on vehicle simulation).

| Group # | Administration day 7 | Administration day 14 | Administration day 21 |
|---|---|---|---|
| 1 | 428 ± 11.2 | 401 ± 8.1 | 425 ± 6.9 |
| 2 | 856 ± 4.2* | 901 ± 16.8 | 907 ± 4.3* |
| 3 | 822 ± 8.7 | 919 ± 4.1* | 922 ± 9.3 |
| 4 | 794 ± 6.9 | 921 ± 9.1 | 928 ± 10.7 |
| 5 | 978 ± 5.1 | 991 ± 0.6 | 979 ± 3.8 |
| 6 | 528 ± 5.8 | 938 ± 11.7 | 947 ± 12.4 |

(*$p < 0.05$ when compared by t-test with the control group 1)
1—the control group;
2—120 mg/kg ascorbate lithium;
3—60 mg/kg ascorbate lithium;
4—30 mg/kg ascorbate lithium;
5—the intact group;
6—60 mg/kg in the form of pills with cocoa.

TABLE 6

Lithium ascorbate effect on aminotransferase and creatinine activity in blood (the test on vehicle simulation)

Amount of aminotransferase and creatinine in blood serum

| Group # | Administration day 7 | | | Administration day 14 | | | Administration day 21 | | |
|---|---|---|---|---|---|---|---|---|---|
| | AST | ALT | Creatinine | AST | ALT | Creatinine | AST | ALT | Creatinine |
| 1 | 41.3 ± 3.10 | 13.2 ± 5.97 | 19.4 ± 2.45 | 40.9 ± 4.92 | 13.5 ± 4.84 | 17.9 ± 5.31 | 42.0 ± 6.17 | 14.0 ± 4.91 | 19.1 ± 2.12 |
| 2 | 107.1 ± 6.20 | 32.4 ± 7.75 | 39.8 ± 6.13* | 110.3 ± 7.41* | 31.7 ± 7.32 | 47.8 ± 1.46 | 118.7 ± 4.48* | 30.1 ± 7.42 | 42.1 ± 2.97* |
| 3 | 97.9 ± 5.04* | 31.0 ± 3.15* | 39.6 ± 7.98 | 112.4 ± 6.23 | 33.1 ± 2.84* | 48.3 ± 8.27* | 115.5 ± 8.97 | 32.4 ± 6.37 | 45.6 ± 2.73* |
| 4 | 91.7 ± 7.29 | 29.8 ± 8.45 | 36.5 ± 3.84* | 109.9 ± 9.67 | 32.1 ± 9.10 | 48.1 ± 3.82 | 121.2 ± 7.21 | 31.7 ± 3.14* | 46.3 ± 3.26 |
| 5 | 129.5 ± 7.33 | 36.3 ± 2.64 | 48.8 ± 4.50 | 131.3 ± 7.48 | 38.1 ± 1.49 | 50.1 ± 4.86 | 128.7 ± 3.26 | 36.9 ± 3.87 | 49.2 ± 4.61 |
| 6 | 68.8 ± 4.72* | 22.7 ± 8.19 | 25.7 ± 4.30 | 119.7 ± 6.21* | 34.8 ± 6.83 | 56.7 ± 6.44* | 121. ± 4.29* | 35.0 ± 4.29 | 58.4 ± 9.30* |

(*$p < 0.05$ when compared by t-test with the control group 1)
1—the control group;
2—120 mg/kg ascorbate lithium;
3—60 mg/kg ascorbate lithium;
4—30 mg/kg ascorbate lithium;
5—the intact group;
6—60 mg/kg in the form of pills with cocoa.

During the accumulation of lithium ascorbate in the body of the experimental animals, the body's response to stress did not proportionally depend on the dose of administration, at least in the ranges of the doses tested. The dose of 30 mg/kg of body weight slightly exceeded the efficacy of the dose of 60 mg/kg. The dose of 120 mg/kg was less effective. Moreover, the $2^{nd}$ and $3^{rd}$ tests (on days 14 and 21 from the start of the study) showed a significant difference between the results obtained at 30 mg/kg and 120 mg/kg dosages, from 3% to 10% on average (Tables 1, 2, 3). Thus, it can be concluded that lithium ascorbate is more effective in small dosages.

Example 4. Efficacy of Prolonged Forms of Lithium Ascorbate

One of the study group was administered the preparation in the form of pills (with cocoa butter as an excipient) at the dosage of 60 mg/kg. This variant suggested a less stressful form of administration and a prolonged, extended type of lithium effects. The obtained results (Table 1-5) suggest that the rate of lithium accumulation was slower in comparison with an aqueous solution of the same dosage administered orally. The activity of this form of administration on the 7th day was lower. But on administration day 14 and day 21, the conditions of animals receiving lithium ascorbate in the form of boluses (pills) with cocoa butter was comparable to that of intact animals and in some cases exceeded the results obtained at oral administration of lithium ascorbate solution. Thus, the effect of prolonged forms is considered to be effective with prolonged exposure and it is characterized by accumulation of lithium ascorbate and a long-lasting beneficial effect on metabolism. An increase in the animal weight in the Group 6 and an increase in blood creatinine indicate an increase in muscle mass. There was no emaciation of the body, which could lead to dystrophy. Adequate response of the body to stresses of various etiologies, accumulation of the body's energy reserve led to an increase in muscle tissue, without a sharp increase in subcutaneous fat (adipose tissue). Thus, the animal grew and developed inspite of stress.

Prolonged, extended-release dosage forms allow for a significant reduction in dosing frequency, thus increasing patient compliance. Smooth and slow release of lithium ascorbate from prolonged dosage forms allows for avoiding sharp increases in lithium blood concentrations and instead provides with uniform lithium blood concentrations for a long period of time, which results in forming effective lithium concentrations in target organs.

Example 5. Determination of Acute Toxicity of Lithium Ascorbate

The parameters of acute toxicity of lithium ascorbate preparation in the form of a solution were studied. The experiments were performed on 4 months old male Wistar rats weighing 180-200 g. The animals were selected and distributed to groups according to the principle of paired analogs, and stayed under identical feeding and housekeeping conditions. Before the beginning of the study, the animals were kept in quarantine for 12 days, and prior to the administration of the compositions they were subjected to deprivation for 24 h. In each series of the experiments, 8 groups of animals were formed with 6 animals in each group.

In the first series of experiments the acute toxicity of lithium ascorbate was determined for oral administration. LD50 (the average lethal dose, i.e. the dose at which 50% of the rats died) was calculated by the Kerber method. The substance was given internally at doses of 1000, 2000, 3000, 4000, 5000, 6000, 7000, 8000 mg/kg of body weight. The volume of the introduced substance was 2.0 ml per rat (the maximum permissible volume for oral administration) intragastrically with a special metal probe. The volume of lithium ascorbate administered to the animals was adjusted with water for injection. The criteria for assessing toxicity were a lethal outcome and the nature of the clinical picture. The data obtained during the experiment on the laboratory animals are presented in Tables 7, 8.

TABLE 7

Determination of median lethal dose of lithium ascorbate in rats (by Kerber)

| Dose, mg/kg | 1000 | 2000 | 3000 | 4000 | 5000 | 6000 | 7000 | 8000 |
|---|---|---|---|---|---|---|---|---|
| Survived | 6 | 6 | 6 | 6 | 5 | 3 | 3 | 0 |
| Dead | 0 | 0 | 0 | 0 | 1 | 3 | 3 | 6 |
| Z | | | | | 0.5 | 2 | 3 | 4.5 |
| D | | 1000 | 1000 | 1000 | 1000 | 1000 | 1000 | 1000 |
| z · d | | 0 | 0 | 0 | 500 | 2000 | 3000 | 4500 |

$\Sigma z \cdot d = 10000$ $LD50 = LD100 - \Sigma(Z*D)/n = 8000 - 1667 = 6333$

LD50 = LD100 − Σ(zd)/n, where LD100 is the dose that caused an effect in all test objects in a group;
D is the interval between two adjacent doses;
Z—the arithmetic mean of the two values of the test object number that showed a positive effect when exposed to each of the two adjacent doses; n is the number of test objects in the group.

TABLE 8

Determination of the median lethal dose of lithium ascorbate in Wistar rats (by Pershin)

| Dose, mg/kg | 1000 | 2000 | 3000 | 4000 | 5000 | 6000 | 7000 | 8000 |
|---|---|---|---|---|---|---|---|---|
| Died/Survived | 0/6 | 0/6 | 0/6 | 0/6 | 1/5 | 3/3 | 3/3 | 6/0 |
| Dead, % | 0 | 0 | 0 | 0 | 16.6 | 50 | 50 | 100 |
| Total dose of standing by, A | | 3000 | 5000 | 7000 | 9000 | 11000 | 13000 | 15000 |
| Difference % of dead, B | | 0 | 0 | 0 | 16.6 | 33.4 | 0 | 50 |
| (A · B) | | 0 | 0 | 0 | 149400 | 367400 | 0 | 750000 |

$\Sigma (A \cdot B) = 1266840$
$LD_{50} = 1266840/200 = 6334$ mg/kg

TABLE 9

Toxicity of lithium salts (per LD50).

| No | Lithium salt | LD50, mg/kg in rats |
|---|---|---|
| | Inorganic salts | |
| 1 | Lithium carbonate | 531 |
| 2 | Lithium fluoride | 175 |
| 3 | Lithium chloride | 970 |
| 4 | Lithium bromide | 2200 |
| 5 | Lithium sulfate | 1190 |
| 6 | Lithium nitrate trihydrate | 1400 |
| 7 | Lithium metatantalate | 750 |
| | Organic salts | |
| 8 | Lithium ascorbate | 6334 |
| 9 | Lithium oxibutirate | 2200 |
| 10 | GABA lithium | 1800 |
| 11 | Lithium citrate | 700 |

TABLE 9-continued

Toxicity of lithium salts (per LD50).

| No | Lithium salt | LD50, mg/kg in rats |
|---|---|---|
| 12 | Lithium succynate | 2416 |
| 13 | Lithium nicotinate | 2200 |
| 14 | Lithium lactate | 2100 |
| 15 | Lithium benzoate | 1200 |

The results of the two methods of determining LD50 confirm the feasibility of any of them, since the differences do not exceed 0.1%, depending on the method taken for the standard. The obtained data made it possible to determine the parameters of acute toxicity of lithium ascorbate. Thus, for white rats of the Wistar line they were: LD50—6334 mg/kg, LD100—8000 mg/kg. So, lithium ascorbate belongs to class 5 of "practically non-toxic" LD50≥5000 mg/kg drugs according to the table of distribution of drugs.

Comparing the doses from 30 mg/kg to 120 mg/kg, in which lithium ascorbate showed an anti-stress and anxiolytic effect, and taking into account the high level of LD50 for lithium ascorbate (6334 mg/kg), we conclude that lithium ascorbate has a wide therapeutic window and low toxicity. In comparison, LD50 of lithium carbonate is 531 mg/kg (Badman A. L., et al, Vredniye khimicheskiye veshchestva: Neorganicheskiye soedineniya elementov of I-IV group, a hand book edited by V. A. Filov et al: Khimiya, 1988. p. 25-26). Moreover, according to the comparison data on toxicity of organic and inorganic lithium salts, lithium ascorbate showed the lowest toxicity in comparison with the other lithium salts (Table 9).

Example 6. Potential Molecular Targets of Lithium Ascorbate

To formulate more detailed mechanisms of biological and pharmacological effects of lithium ascorbate, we made the analysis of possible interactions between lithium ions and human proteome proteins. The searches in human proteome databases (NCBI PROTEIN, EMBL, UNIPROT, Human Proteome Map (HPM), BIOCYC-HUMAN, etc.) have shown that the human proteome contains at least 47 proteins which activity may be controlled in one way or another by lithium ions. The list of 47 lithium dependent proteins (including transport proteins of Li+ ion) was analyzed with the functional binding method (Torshin I. Yu. Nova Biomedical Books, NY, USA, 2009, In "Bioinformatics in the Post-Genomic Era" series, ISBN 1-60692-217-0). The analysis of functional interrelations—one of the information technologies of modern bioinformatics.

As a result of the analysis, among known 50057 human proteome proteins, 20180 annotated proteome proteins were specified (i.e. proteins which principal biological roles are at least known). Among 20180 proteins, 47 proteins are related in one way or another with biological lithium roles. Among the list of 47 proteome proteins which activity is interrelated with lithium ions in one way or another, the proteins were isolated which activity depends on lithium ions directly or indirectly, and which modulate concurrently metabolism of neurotransmitters and activity of neurotransmitter receptors providing normothimic effects of lithium ascorbate (Table 10).

TABLE 10

Lithium-dependent proteins interrelated with neurotransmitter metabolism modulation and activity of neurotransmitter receptors.

| Gen(s) | Protein (proteins) | Protein/gene function | Lithium roles |
|---|---|---|---|
| ADCY5 | Adenylate-cyclase 5 | Synthesis of signal molecule cAMP during intracellular signalling through G-proteins | Inhibits a catalytic subunit of adenylate cyclase 5 |
| TPH2 | Tryptophan-5-hydroxylase 2 | Biosynthesis of serotonin from L-tryptophan | Decrease of TPH2 expression, increase of serotonin secretion |
| PTK2B | Tyrosine kinase 2-beta | Regulation of NMDA receptors, activation of PI3K, signal cascades AKT1, ERK2, ERK1 | Lithium suppresses physphorylation of remnant tyrosine-402 which promotes inactivation of NMDA receptor |
| GRIA1, GRIA3, etc. | Glutamate receptor GluR | Metabotropic glutamate receptors | Decrease of levels of glutamate receptor GluR1 |
| SLC38A1 | Na-coupled transporter 1 of neutral amino acids | Provision of glutamatergic and GABAergic neurons by glutamine for glutamate and GABA synthesis | It is inhibited by lithium ions |
| SLC8B1 | Mitochondrial Na/K/Ca exchanger 6 | Lithium-calcium exchange, Ca forwards to mitochondria, Li-within cell | Activation of transport of Ca2+ ions within mitochondria, suppression of excitotoxicity |
| ASIC1 | Acid-sensing ion channel 1 | Post-synaptic proton receptor, modulates activity of neural networks | Transport of Li+ ions |

There are available literature data showing potential molecular mechanisms behind the claimed lithium ascorbate effects. Among the proteins enlisted in Table 10, Adenylate cyclase-5 is presumed to be the most important target protein for normothimic effects of lithium ascorbate.

It was shown that the Li+ ion interacts immediately with catalytic subunit of adenylate cyclases [Mork A, Geisler A, Pharmacol Toxicol. 1987; 60(4):241-248]. Lithium inhibits to a larger extent adenylate cyclase-5 (on 50%) and adenylate cyclase-7 (на 40%) which are activated with stimulation of D1 dopamine receptors. The inhibition of these adenylate cyclases promotes implementation of mood-stabilizing effects of lithium [Mann L, Heldman E et al, Neuropsychopharmacol 2008; 11(4):533-9 doi]. Moreover, lithium ions not only inhibit adenylate cyclase-5 mediating effects of the dopamine receptor but also modulate dopamine levels in various brain regions [Maggi et al, J. Neurochem. 1980; 34, 888-892; Corrodi et al, Psychopharmacologia, 1967; 11, 345-353; Friedman et al, Nature, 1973; 243, 520-521]. Adenylate cyclases also mediate signal cascades of adrenoreceptors [Chen Y, Friedman J et al, Ann Neurol. 2014; 75(4):542-9 doi] therefore the immediate inhibition of adenylate cyclases of lithium ions also suppresses adrenergic neurotransmission. Lithium also increases activity of serotoninergic neurotransmission [Haddjeri N, Szabo S T et al, Neuropsychopharmacol 2000; 22(4):346-356]. Moreover, a short-term (8 h) and long-term (14 days) exposure to 1 mM of lithium on serotoninergic neurons in the culture results in the increase of serotonin secretion on 20% [Scheuch K, Holtje M et al, Brain Res. 2010; 1307:14-21 doi]. Hereby exposed to lithium, the selective tryptophan absorption in synaptosomes of the striatal nerve on 40% activation of serotonin biosynthesis from tryptophan occur. The increase of serotonin secretion exposed to lithium is consistent with the regulation of serotonin biosynthesis per the feedback mechanism from 5-HT1 receptors [Knapp S, Mendel A J, J Pharmacol Exp Ther. 1975; 193(3): 812-823].

Therefore, the inhibition of adenylate cyclase-5 by lithium ions contained in lithium ascorbate may explain a normothymic effect of lithium salts as mediated by a "fine-tuned" modulation of dopaminergic, adrenergic and serotoninergic systems. Lithium inhibition of adenylate cyclases promotes suppression of dopaminergic and adrenergic neurotransmission concurrently enhancing serotinergic signals.

Normothimic Roles of Ascorbate-Anion

The ascorbate-anion presented in lithium ascorbate increases bioavailability of lithium ions and promotes enhance lithium accumulation in the nerve tissue. Along with marked antioxidant properties of ascorbate-anion (Vitamin C) and its target accumulation in brain and neuroendocrine tissues (adrenal glands), ascorbate-anion modulates activity of dopaminergic, serotoninergic, GABAergic, glutamatergic neurotransmission. The potential use of vitamin C for treatment of schizophrenia, principal depressive disorder, bipolar disorder has been shown [Moretti M, Fraga D B, Rodrigues A, CNS Drugs. 2017 July; 31(7):571-583].

It was established in the experiment that the action of ascorbate-anion is opposite to behavioral dopamine effects [Rebec, Pierce, Prog Neurobiol. 1994; 43(6):537-65]. In another experiment, ascorbic acid showed antidepressive effect and was able to decrease significantly depression-like behavior induced by acute stress [Moretti et al., J Mol Neurosci. 2013; 49(1):68-79] and chronic unexpected stress [Moretti et al., J Psychiatr Res. 2012; 46(3):331-40] with the efficacy similar to the one of conventional antidepressants (fluoxetine).

Antidepressive Effect of Ascorbate-Anion is Related to Dopamine and Serotonin Metabolism.

Moreover, ascorbate-anion is necessary for recirculation of tetrahydrobiopterine which is the cofactor of enzymes tyrosine hydoxylase (synthesis of catecholamines) and tryptophan hydroxylase (synthesis of serotonin) [Taylor et al., Cell Signal. 2005; 17(5):549-57].

In the experiment, haloperidol administration prior exposure to ascorbic acid has prevented an antidepressive effect of ascorbate-anion which indicates involvement of dopaminergic system in the antidepressant-like action of the compound via modulation of activity of dopamine D2-receptors [Binfare et al., Prog Neuropsychopharmacol Biol Psychiatry. 2009; 33(3):530-40]. The same study has shown that an antidepressant effect of ascorbic acid also includes activation of serotonin receptors 5-HT1A, 5-HT2A/2C and 5-HT3.

Therefore, available literature data suggest potential for synergistic effect of combination of lithium ion and ascorbate ion for alleviating stress-related and depression-like symptoms. Lithium effects via inhibition of adenylate cyclase-5 are related to suppression of dopaminergic and adrenergic neurotransmission, and administration of ascorbate-anion results in the similar effects. Thus, both agents are acting by different mechanisms, but in the same direction, providing possibility for their combination to have a synergistic effect.

Example 7. Chemoinformation Analysis of Lithium Salts

Lithium salts differ significantly in their pharmacokinetic and other biological properties that leads to considerable differences in their bioavailability and pharmacological action. Inorganic salts (chloride, carbonate) due to comparatively small anion sizes, in principle, may not show highly specific interactions with proteome proteins or other macromolecules. As a result, intracellular transport of lithium ions is significantly complicated, and the larger part of lithium ions is diffused in intercellular fluid.

Unlike inorganic salts, salts with organic salts anions (ascorbate, nicotinate, oxibutirate, etc.) which may interact more specifically with proteins, provide more effective intracellular transport of lithium ions and, may, as a result, show tissue-specific effects.

The chemoinformation analysis allows to find molecules similar to the test one and, respectively, suggest physiological, pharmacological and other properties of the test molecule based on the available information on properties of molecules, most similar per the structure. The specific subsection of chemoinformatics, chemoreactome analysis, is aimed to assess biological activities of the test molecule (in particular, modeling of affinity profile of the test molecular structure to various proteome proteins).

Using the chemoinformation analysis, we compared the chemical structure of ascorbate and molecules in the database of human metabolome and molecules in the drug databases. As a model of human metabolome, more than 40000 compounds were used which are presented in database HMDB (Human Metabolome Database, i.e. database of human metabolome).

During the chemoreactome modeling, over 500.000 biological activities of over 10.000.000 molecules which information was presented in database PubChem were analyzed. From the obtained list of 4520 biological activities, those were chosen which differences in assessment values differed for ascorbate in comparison with control molecules—nicotinate and oxibutirate.

As a result, the assessments of various anion properties were made for the ascorbate, nicotinate, oxibutirate and carbonate salts: neurophysiologic, vasoactive, hemodynamic, anti-inflammatory and others. The results of ascorbate modeling are presented in comparison with the control salts (nicotinate, oxibutirate and carbonate).

Chemoreactome Analysis of Neurophysiologic Properties of Ascorbate

The chemoreactome modeling showed that the larger affinity to serotonin, dopamine, benzodiazepine, adrenergic and other receptors is more common for ascorbate-anion in comparison with nicotinate, oxibutirate and carbonate (see Table 11, 12). The higher affinity to receptors shows, first, possible modulation of activity of these receptors by lithium ascorbate and, second, more intensive transport of lithium ascorbate within neurons (during internalization of cell membrane receptors).

The analysis showed higher affinity of ascorbate to human serotonin receptors 5HT1A, 5HT2B, 5HT6 (in comparison with the affinity of nicotinate, oxibutirate). 5HT1A receptors regulate a wide range of CNS functions including aggression, anxiety, appetite, blood pressure, HR, memory, nociception, "sleep-wake" cycle, thermal regulation. 5HT2B receptors regulate anxiety, appetite, GIT motility, vasoconstriction, and 5HT6 receptors—anxiety, cognitive abilities, learning, memory. The higher inhibition of SHTT absorption ($K_i$=872 nM, in the submicromolar range typical for drugs) indicate possible effects of ascorbate lithium as a selective serotonin reuptake inhibitor (SSRIs) which are used for treatment of anxiety disorders and depression.

The higher, in comparison with nicotinate, oxibutirate and carbonate, affinity of ascorbate-anion to human benzodiazepine receptors shows possible anxyolitic ascorbate effect.

The conclusion is confirmed by the results of modeling of interaction with NMDA-receptors and other glumatic receptors—ascorbate will promote inhibition of activity of NMDA-receptors NR1a/NR2D (Ki=622 nM) and human metabotropic receptors mGluR1a (Ki=47 nM). Glutamate receptors maintain processes of CNS excitation so their inhibition corresponds to sedative and anxyolitic effects.

It should be mentioned that ascorbate may be more effective than nicotinate and oxibutirate (see Table 11, 12) in inhibition of activity GSK3B enzyme (ascorbate—47%, nicotinate—3.3%, oxibutirate—6%)—one of the main target proteins of lithium ion exposure. The inhibition constant of GSK3B (IC50) was 13.2 nM for ascorbate, 2534 nM for nicotinate and 1658 nM for oxibutirate. In other words, ascorbate-anion has the largest inhibition potential of GSK-3, and nicotinate—the lowest. The result is partially confirmed by the results of the modeling of GSK3B phosphorylation via AKT1—the value of inhibition constant IC50 was 3890 nM for ascorbate and was higher for nicotinate (6835 nM).

TABLE 11

Binding with neurotransmitter receptors and other neurological effects of ascorbate in comparison with nicotinate and lithium carbonate (per the results of test pharmacological constant based on the results of the chemoreactome analysis).

| Const. | Ascorbate | Nicotinate | Carbonate | Err. | U | Activity |
|---|---|---|---|---|---|---|
| | | | | | | Serotonin receptors |
| Ki | 173.1 | 1050 | 5400 | 314 | nM | Affinity to hyppocampal receptor 1A 5-hydroxytryptamine, ligand 8-OH-DPAT |
| Ki | 648 | 2980 | 8850 | 872 | nM | Inhibition of 5HTT absorption, ligand cytalopram |
| Ki | 120.1 | 1378 | 6300 | 394 | nM | Affinity to human 5HT2B receptors, ligand LSD |
| Ki | 263.4 | 604 | 10045 | 319.6 | nM | Substitution of LSD from human receptor 5-HT6 |
| | | | | | | Dopamine receptors |
| Ki | 1164 | 2564 | 7340 | 397.8 | Bi | Affinity to dopamine receptors D1 in the rat striatum, ligand phenoldopame |
| Ki | 26.28 | 421.8 | 3450 | 559 | nM | Affinity to human dopamine receptors D3, ligand spiperone |
| | | | | | | Benzodiazepine receptors |
| Ki | 343.9 | 4344 | 9284 | 972 | nM | Affinity to benzodiazepine receptors, ligand diazepam |
| Ki | 248 | 591 | 4829 | 213.6 | nM | Flumazenil substitution from the central benzodiazepine receptor of human cortical membranes |
| | | | | | | Glutamate receptors |
| Ki | 622 | 1866 | 7402 | 319.6 | nM | Inhibition of currents of N-methyl-D-aspartate receptors NR1a/NR2D |
| IC50 | 47 | 614.6 | 4356 | 95.09 | nM | Inhibition of human receptor mGluR1a via measurement intracellular calcium |
| | | | | | | Adrenergic receptors |
| Ki | 173 | 438.7 | 6820 | 182.1 | nM | Affinity to alpha-2 adrenergic receptors of rat brain homogenates, ligand clonidine |
| Ki | 547 | 1883 | 6029 | 655 | nM | Affinity to alpha-1 adrenergic receptors of the rat cortex, ligand prazosin |
| | | | | | | Acetyl choline receptors |
| Ki | 115 | 1838 | 5928 | 2539 | nM | Substitution of N-methylscopolamine from muscarine receptors M1 |
| | | | | | | GSK3 inhibition |
| — | 47 | 3.3 | 0 | 6.7 | % | GSK3B inhibition at 1 µM |
| IC50 | 13.2 | 2534 | 8240 | 191 | nM | Inhibition constant GSK3B |
| IC50 | 3890 | 6835 | 13014 | 6011 | nM | Inhibition of GSK3B phospholyration via AKT1 |
| | | | | | | Modeling of experimental effects |
| — | 46.45 | 1.804 | — | 23.98 | % | % of relief of amnesia induced by electric shock in the rat experiment in dose 10 mg/kg i/m |
| — | 60.4 | 111.1 | — | 81.59 | mg/kg | Anticonvulsant activity in the electric shock model |

"Const.", a common name of the test pharmacological constant type ("Ki", "IC50", etc.);

"Err."—the error of assessed properties;

"U", measurement units.

TABLE 12

Binding with neurotransmitter receptors and other neurological effects of ascorbate in comparison with nicotinate and lithium carbonate (per the results of the chemoreactome analysis).

| Const. | Ascorbate | Oxibutirate | Err. | U. | Activity |
|---|---|---|---|---|---|
| | | | | | Serotonin receptors |
| Ki | 220.9 | 1261 | 12.19 | nM | Affinity to 2 5-hydroxytriptamine receptor in the frontal cortex of rats |
| Ki | 37.57 | 339.5 | 0.0475 | nM | Affinity to 5-HT7b receptor, ligand 5-CT |
| Ki | 11.98 | 1344 | 67.2 | nM | Affinity to 5-HT1A, ligand 8-OH-DPAT |
| Ki | 263.4 | 1503 | 319.6 | nM | Affinity to 5-HT6, ligand LSD |
| | | | | | Opioid receptors |
| Ki | 44.96 | 187.7 | −2.29 | nM | Affinity to rat delta-1 opioid receptors, ligand Ile5, 6-deltorphin-2 |
| Ki | 146.6 | 1474 | −23.19 | nM | Affinity to human mu-opioid receptors |
| — | 233.9 | 882 | 29.87 | nM | Antagonism of mu-opioid receptors, ligand GTP-gamma-S |
| — | 31 | 837 | 26.35 | — | Selectivity of antagonism of mu-opioid receptors in comparison with kappa receptors |
| | | | | | Cannabinoid receptors |
| Ki | 346 | 1067 | 1263 | nM | Affinity to human CB2 receptors, ligand CP-55940 |
| Ki | 652.8 | 3693 | −1.114 | nM | Affinity to CB2 receptors, ligand CP-55940 |
| | | | | | Benzodiazepine receptors |
| Ki | 343.9 | 499 | 972 | nM | Affinity to benzodiazepine receptor, ligand diazepam |
| Ki | 135 | 212.4 | 213.3 | nM | Affinity to central benzodiazepine receptors, ligand flumazenil |
| | | | | | Dopamine receptors |
| Ki | 102 | 285.4 | −41.35 | nM | Affinity to human dopamine receptors D2L |
| Ki | 268.4 | 3170 | 68.59 | nM | Affinity to dopamine receptors D1, ligand SCH23390 |
| IC50 | 176.4 | 648 | 221 | nM | Affinity to dopamine receptor D2, ligand YM09151 |
| | | | | | Glutamate receptors |
| Ki | 622 | 930 | 319.6 | nM | Inhibition of currents of N-methyl-D-aspartate receptors NR1a/NR2D |
| IC50 | 214 | 426 | 90.2 | nM | mGluR1a antagonism via measurement of intracellular calcium |
| EC50 | 1186 | 2784 | −256 | nM | Inhibition of metabotropic glutamate-receptor-2 |
| | | | | | Other |
| — | 16.03 | 28.3 | −3.666 | % | Partial agonism of adrenergic beta-2 receptors as cAMP synthesis at 30 μm |
| EC50 | 169.6 | 30.7 | −17.3 | nM | Agonist of beta-1 receptors as cAMP accumulation |
| — | 47.96 | 0.09319 | 6.796 | % | GSK3B inhibition (1 μm) |
| IC50 | 13.2 | 1658 | 158.6 | nM | Inhibition constant GSK3-beta |

"Const.", a common name of the test pharmacological constant type ("Ki", "IC50", etc.);
"Err."—the error of assessed properties;
"U", measurement units.

Chemoreactome Modeling of Pharmacokinetic and Pharmacodynamic Properties of Ascorbate It is known that ascorbic acid is absorbed predominantly in small intestines, TCmax after oral administration—approximately 4 h. With the dose increase up to 200 mg, it is absorbed up to 140 mg (70%); with the further dose increase, absorption is decreased (50-20%). The binding with plasma proteins—25%. In normal settings, plasma concentration of ascorbic acid is about 10-20 μg/ml.

The analysis allows to get comparative assessments of ascorbate pharmacokinetic properties (Table 13, 14). Ascorbate solubility is higher than the one of nicotinate and lithium oxibutirate. The prediction of ascorbate properties showed that the administration of even high doses of ascorbate (about 10 mg/kg/day), despite of nicotinate and oxibutirate, will not result in significant hematocrit change (related to the changes in water-salt balance of blood corpuscles): the obtained assessment implies a rather small percentage of hematocrit change—3.8%.

Ascorbate-anion is a highly effective antioxidant. Therefore, ascorbate is metabolized and eliminated more rapidly than comparator molecules. The assessments of such pharmacokinetic characteristics as T1/2 in liver microsomes (0.14 h, i.e. 10 min) and clearance were higher for ascorbate (ascorbate—29 ml/min, nicotinate—19 ml/min, oxibutirate—21 ml/min, Tables 13, 14). Clearance—the rate of the study substance removal from the body while it is biotransformed and eliminated from the body.

TABLE 13

Assessments of vasoactive and hemodynamic properties of ascorbate in comparison with nicotinate and lithium carbonate (per the results of the chemoreactome analysis).

| Const. | Ascorbate | Oxibutirate | Carbonate | Err. | U. | Activity |
|---|---|---|---|---|---|---|
| IC50 | 395.8 | 1447 | >20000 | 813 | nM | Inhibition of purified human rennin |
| Ki | 145 | 2389 | >25000 | −731 | nM | Affinity to vasopressin receptors V1B, ligand AVP |
| IC50 | 125.7 | 383 | >40000 | −507 | nM | Inhibition of blood coagulation factor 10a |
| IC50 | 627.6 | 1308 | 12080 | 3590 | nM | Inhibition of platelet-derived activation factor, ligand PAF |
| — | −58 | −26.26 | 0 | −46.64 | % | Percentage change of total cholesterol during experimental diet "cholesterol + peanut butter" |
| — | 91.2 | 53.29 | 0 | 7.83 | % | Antioxidant activity per the levels of peroxyl radicals measured by spectrophotometry in formazon formation |
| IC50 | 338 | 1751 | 91230 | 36.18 | nM | Affinity to PPAR-gamma receptor |
| EC50 | 26.3 | 2264 | 82303 | 294.8 | nM | PPAR-delta agonist |
| — | 14.98 | 8.08 | 0 | 5.517 | % | Anti-hyperglycemic activity in rats as the decrease of glucose level in dose 100 mg/kg, per os |

"Const.", a common name of the test pharmacological constant type ("Ki", "IC50", etc.);
"Err."—the error of assessed properties;
"U", measurement units.

TABLE 14

Assessments of vasoactive and hemodynamic ascorbate properties in comparison with oxibutirate (per the results of the chemoreactome analysis).

| Const. | Ascorbate | Oxibutirate | Err. | U. | Activity |
|---|---|---|---|---|---|
| — | 8.81 | 24.75 | −15.77 | % | BP exposure in rats under anesthesia |
| IC50 | 395.8 | 1204 | 813 | nM | Renin inhibition |
| — | 93 | 144.5 | 24.35 | μmol | Antioxidant activity against copper-induced lipid peroxidation |
| EC50 | 1238 | 5088 | −1208 | nM | Vasodilator activity of thoracic aorta as the inhibition of L-phenylephrine-induced contraction |

"Const.", a common name of the test pharmacological constant type ("Ki", "IC50", etc.);
"Err."—the error of assessed properties;
"U", measurement units.

Example 8. Comparison of Efficacies of Lithium Ascorbate and Lithium Carbonate after Low Dose Administration in Rats Behavioral tests in rats (Porsolt helplessness test) show significantly higher efficacy of lithium ascorbate in a low dose (5 mg/kg) in comparison with the placebo group and positive control group (Phenazepam) on dosing day 7 and 28 (Table 15). The data show the absence of lithium carbonate activity in the dose (5 mg/kg) that is the same as in the placebo group.

The second part of the experiment demonstrates the preservation of specific activity of lithium ascorbate after the drug withdrawal in 7 and 28 days, and, respectively, the absence of the effect for lithium carbonate (Table 16).

TABLE 15

Effect of lithium ascorbate and carbonate on rat behavior in the Porsol ttest.

| Groups | Duration of activity (sec) | Duration of immobility (sec) | Number of gastric ulcers | Eosinophils (Dunger method) in mm$^3$ | Adrenalin μg/l | Noradrenalin μg/l |
|---|---|---|---|---|---|---|
| 7 days after the dosing | | | | | | |
| 1 group (placebo) | 107.3 ± 23.7 | 492.7 ± 84.6 | 5.4 ± 1.8 | 307.6 ± 23.7 | 24.4 ± 5.3 | 68.6 ± 12.3 |
| 3 group LiAsc (5 mg/kg) | 356.4 ± 26.1* | 243.6 ± 17.6* | 1.5 ± 0.6* | 783.2 ± 24.7* | 7.4 ± 1.4* | 19.9 ± 0.9* |
| 7 group LiCa (5 mg/kg) | 100.9 ± 64.9 | 499.1 ± 53.0 | 5.9 ± 2.1 | 312.6 ± 68.1 | 24.9 ± 9.5 | 69.3 ± 35.2 |
| 10 group (0.25 mg of phenazepam) | 426.7 ± 76.4 | 173.3 ± 22.1* | 0.4 ± 0.1 | 969.1 ± 42.3 | 6.8 ± 0.65 | 17.6 ± 1.95 |
| 28 days after the dosing | | | | | | |
| 1 group (placebo) | 93.6 ± 11.1 | 506.0 ± 94.3 | 7.3 ± 2.9 | 301.3 ± 25.1 | 31.2 ± 6.1 | 74.9 ± 12.10 |
| 3 group LiAsc (5 mg/kg) | 506.4 ± 31.4* | 93.0 ± 19.3* | 0.8 ± 0.2* | 987.3 ± 34.8* | 6.1 ± 0.6* | 15.6 ± 0.79* |

TABLE 15-continued

Effect of lithium ascorbate and carbonate on rat behavior in the Porsol ttest.

| Groups | Duration of activity (sec) | Duration of immobility (sec) | Number of gastric ulcers | Eosinophils (Dunger method) in mm$^3$ | Adrenalin μg/l | Noradrenalin μg/l |
|---|---|---|---|---|---|---|
| 7 group LiCa (5 mg/kg) | 90.8 ± 67.3 | 508.9 ± 107.2 | 7.3 ± 2.6 | 301.8 ± 102.3 | 36.7 ± 9.6 | 76.83 ± 30.2 |
| 10 group (0.25 mg of phenazepam) | 494.8 ± 60.4 | 105.2 ± 20.1 | 0.1 ± 0.2 | 988.1 ± 42.3 | 6.2 ± 0.57 | 16.2 ± 1.1 |

LiAsc—lithium ascorbate;
LiCa—lithium carbonate.
(*p < 0.05 as compared with the control group 1 using t-test)

TABLE 16

Effect of lithium ascorbate and carbonate on rat behavior in the Porsolt test in 7 and 28 days after the withdrawal.

| Groups | Duration of activity (sec) | Duration of immobility (sec) | Number of gastric ulcers | Eosinophils (Dunger method) in mm$^3$ | Adrenalin μg/l | Noradrenalin μg/l |
|---|---|---|---|---|---|---|
| 7 days after the drug withdrawal | | | | | | |
| 1 group (placebo) | 91.3 ± 13.6 | 508.7 ± 67.8 | 8.4 ± 3.4 | 289.4 ± 46.1 | 34.3 ± 12.4 | 76.1 ± 22.3 |
| 3 group LiAsc (5 mg/kg) | 472.6 ± 29.3* | 127.3 ± 19.7* | 1.6 ± 0.9* | 923.5 ± 64.2* | 8.4 ± 0.9* | 18.3 ± 3.2* |
| 7 group LiCa (5 mg/kg) | 91.8 ± 43.9 | 507.9 ± 101.4 | 9.9 ± 3.7 | 299.3 ± 93.5 | 29.6 ± 13.6 | 80.6 ± 29.7 |
| 28 days after the drug withdrawal | | | | | | |
| 1 group (placebo) | 90.9 ± 19.8 | 509.1 ± 102.3 | 9.3 ± 2.9 | 284.3 ± 39.6 | 33.2 ± 22.6 | 75.4 ± 34.6 |
| 3 group LiAsc (5 mg/kg) | 221.1 ± 19.8* | 377.9 ± 86.4* | 5.9 ± 0.4* | 409.7 ± 37.9* | 20.3 ± 9.3* | 38.9 ± 10.9* |
| 7 group LiCa (5 mg/kg) | 93.8 ± 32.7 | 504.4 ±173.4 | 10.0 ± 4.8 | 281.2 ± 83.1 | 37.1 ± 14.7 | 76.34 ± 18.6 |

LiAsc—lithium ascorbate;
LiCa—lithium carbonate.
(*p < 0.05 as compared with the control group 1 using t-test)

Example 9. Investigation of Efficacy of a Preferred Lithium Ascorbate Composition in a Pilot Clinical Trial Effects of lithium ascorbate in a preferred composition according to the present invention on stress and anxiety during phychoemotional stress conditions (during examination period) were investigated in a pilot, open label clinical trial.

Sixty young people, the students of the Ivanovo State Medical Academy aged 19 to 25 years in the two compared groups have taken part in the study. The study subjects were selected based on collection of medical histories and copying out data from the medical histories. The study exclusion criteria were the presence of severe, acute and chronic somatic, psychiatric diseases, administration of any drugs and food supplements.

The composition of active substances (in tablets) used in the study was as follows: lithium ascorbate—6.36 мΓ—68% (mass %); thiamine mononitrate (one of the possible forms of vitamin B1; an alternative form, thiamin hydrochloride, could also be used)—1.2 мΓ—13%; pyridoxine hydrochloride (one of the possible forms of vitamin B6; an alternative form, pyridoxine 5'-phosphate, could also be used)—18 мΓ—19%. The first group included 30 subjects taking the therapy with the experimental composition (EC), 1 tablet thrice a day for 8 weeks (60 days). The young people in the second, control group (30 subjects) participated in the study without taken any drug therapy. All young people had the triple examinations to assess anxiety and depression levels (1-st, baseline—"day 0" and 2-nd, in 30 study days—"day 30", and upon the study completion—"day 60").

Methods for Assessment of Anxiety and Depression Levels.

Anxiety and depression levels were assessed per the Hospital Anxiety and Depression Scale (HADS) and the Hamilton Rating Scale for Depression (1960).

The statistical processing was made with the use of Statistica 10.0. Using the pooled data, we calculated the mean arithmetic of variation range (M) and the mean arithmetic error (in). The Student's test was used for intergroup comparisons, the significance of intergroup differences of values was determined per the paired T-Wilcoxon test. The values of patient distribution by the element status were assessed using non-parametric criterion $c^2$ for independent empirical group distributions. The degree of freedom between individual values was determined per the correlation coefficients (r) using the parametric Pearson methods, and on small samples using the Spearman rank correlation coefficient. The differences were considered significant at the significance level over 95% ($p<0.05$).

Effect of Lithium Ascorbate (in the Experimental Composition) on Anxiety and Depression Levels The baseline depression level was assessed per the Hamilton Rating Scale for Depression. When the assessment was made on day 0 in the compared groups, depression level corresponded to a mild depressive disorder (Table 17). In the students taking the therapy with the experimental composition, the composite score significantly improved on study days 30 and 60 per the Hamilton Rating Scale for Depression and was within the normal range. Meanwhile the score of the students in the control group per the Hamilton scale did not change.

TABLE 17

Dynamics of anxiety and depression levels in group 1 (Experimental composition (EC)) and control group, M ± m

| Main parameters for assessment of depression and anxiety levels | Fine scores | | | | | |
|---|---|---|---|---|---|---|
| | day 0 | | day 30 | | day 60 | |
| | group 1 EC | group 2 control | group 1 EC | group 2 Control | group 1 EC | group 2 Control |
| Assessment of anxiety level per the Hospital Anxiety and Depression Scale (HADS) | 6.49 ± 0.41 | 6.65 ± 0.3 | 4.81 ± 0.49# | 6.83 ± 0.9 | 4.23 ± 0.65# | 6.71 ± 0.6 |
| Assessment of depression level per the Hospital Anxiety and Depression Scale (HADS) | 6.69 ± 0.43 | 6.54 ± 0.33 | 5.46 ± 0.37# | 6.89 ± 0.49 | 5.23 ± 0.41# | 6.94 ± 0.1 |
| Assessment of depression level per the Hamilton Rating Scale for Depression | 9.66 ± 0.88 | 10.23 ± 0.7 | 6.35 ± 0.74# | 10.86 ± 0.3 | 5.88 ± 0.9# | 10.79 ± 0.94 |

Remark.
significant changes on study days 0, 30 and 60 in group 1 taking EC, $p < 0.05$, (Student's test).

When the baseline depression and anxiety levels were assessed per HADS scale, the absence of significantly shown anxiety and depression symptoms was determined (Table 17). In the students taking Normotim therapy, the composite score of anxiety, depression was considerable increased on study days 30 and 60, the mood was improved per the HADS scale and was within the normal range. Meanwhile the composite score of the HADS score did not change.

The obtained results show the anti-stress, antidepressant, anti-anxiety activity of the study drug in young people which is related to neuroprotective properties of lithium ascorbate in the experimental composition.

Concluding Remarks.

Summing up the abovementioned, the results of the experiments made by the authors showed the significant superiority and uniqueness of properties of lithium ascorbate in comparison with other lithium salts which suggests that lithium ascorbate should be reviewed and assessed as an individual compound, rather than the one of lithium salts.

The high efficacy of lithium ascorbate in comparison with other available lithium salts may be explained by a synergic effect of lithium ion and ascorbate anion. Each of them has their own psychoneurological effects (with several modes of action that can be traced back to the molecular targets); their effects are unidirectional and potentiate each other, creating a stable synergy.

The abovementioned effects have been confirmed by several experiments disclosed in the current Description by the authors and can be summarised as follows:

1) Lithium ascorbate has the lowest toxicity among the common lithium salts investigated by the authors (Example 5, Tables 7, 8 and 9);

2) Ascorbate anion and lithium ascorbate have different mechanisms but affect unidirectionally dopaminergic, adrenergic and serotonergic system enhancing efficacy of each other (Example 6, Table 10);

3) The chemoreactome analysis showed that lithium ascorbate has the largest affinity to dopamine, serotonin, benzodiazepine, adrenergic brain receptors compared to lithium carbonate, lithium oxibutirate, lithium carbonate and lithium nicotinate. That, in its turn, suggests a greater anxyolitic, antidepressant, normothymic and neuroprotector activity of lithium ascorbate (Example 7, Table 11-14);

4) Behavioral tests (Porsolt helplessness) revealed a high specific activity of lithium ascorbate, while lithium carbonate in the same dosages showed zero activity (Example 8, Table 15-16);

5) The clinical studies on stress resistance, anxyolitic and antidepressant properties (based on the experimental composition) proved the high efficacy of the lithium ascorbate composition in the low dose applications (Example 9, Table 17).

The examples of the compositions based on lithium ascorbate are disclosed below. The following examples do not limit the applicability of the present invention, but merely illustrate the options of its implementation.

Example 10

We used a composition containing lithium ascorbate and vitamins: pyridoxine hydrochloride—B6, and thiamine mononitrate—B1 in an aqueous solution in different percentage ratios. The antistress, anxiolytic and antidepressant efficacies of the compositions with different ratios of lithium ascorbate and vitamin B1 and B6 were determined.

Four groups of animals were formed. The compositions were administered orally in an aqueous solution. The concentrations of the ratios were as follows: Group (1) received 10% ascorbate lithium, 55% of vitamin B6 and 35% of vitamin B1; Group (2)—50% of ascorbate lithium, 30% vitamin B6 20% vitamin B1; Group (3)—65% of lithium ascorbate, 20% of vitamin B6 and 15% of vitamin B1; Group (4)—90% of the lithium ascorbate, 6% of vitamin B6 and 4% of vitamin B1; Group (5)—the control group received only water for injections.

Neuropsychiatric agitation implies the character and intensity of the movement of the animal in the arena. It depends on various stress factors (e.g., unusual environment for an animal) in combination with natural exploratory activity and is used for the diagnostics of the functional condition of the nervous system when exposed to natural and experimental environmental factors. The indicators of increased anxiety and stress are the number of boluses and acts of grooming, the level of exploratory activity, mobility, and the levels of curiosity or general apathy, which correlate with the level of depression. The performed tests showed that the studied parameters correlated well with the results of other behavioral tests.

Male white Wistar rats weighing 130-170 g were used as model objects. The animals were kept in the identical rooms in cages for 10 rats each at the temperature of 19-21° C. The animals were fed daily with mixed fodder, 30-40 g per each. The water was available without restriction. Forty animals were involved in the study. The animals were divided into four groups of 10 animals in each. The composition was administered for 5 days. The animal behavior was investigated in the "Open field" test. The animals were placed in an open field (a pilot site) after 5 day administration. The animals were placed in the same square, located near the wall. The exposure time of each animal model was 5 minutes.

TABLE 18

Effect of composition on the behavior of rats in the "Open field" test after 5 days of administration

| Group | Vertical motor activity | Horizontal motor activity | Number of peepings in a hole | Number of grooming acts | Number of comings to a central zone | Numer of boluses |
|---|---|---|---|---|---|---|
| 1 | 17.24 ± 4.86* | 5.56 ± 1.24 | 4.76 ± 2.41 | 17.25 ± 3.61 | 1.21 ± 1.82 | 5.14 ± 0.23 |
| 2 | 27.32 ± 2.87 | 6.18 ± 0.42 | 9.32 ± 3.13 | 9.43 ± 4.12 | 3.12 ± 2.17 | 2.12 ± 0.48 |
| 3 | 29.46 ± 3.74 | 6.75 ± 0.68 | 9.98 ± 0.96* | 8.44 ± 4.76 | 2.84 ± 0.14 | 2.54 ± 0.68 |
| 4 | 21.09 ± 1.95 | 7.78 ± 0.46 | 5.85 ± 0.96* | 11.68 ± 4.76 | 1.69 ± 0.14 | 4.83 ± 0.24 |
| 5 | 7.21 ± 2.75 | 3.48 ± 0.75 | 2.96 ± 0.42 | 23.47 ± 2.38 | 0.9 ± 0.42 | 6.46 ± 0.16 |

The obtained results show that: 1) the composition exhibits the mentioned activity at comparing the results obtained in the experimental and control groups; 2) the effective range of the active agent ratios in the composition is quite wide, but the maximum efficacy of the composition is achieved at the ratio of 65% of lithium ascorbate, 20% of vitamin B6 and 15% of vitamin B1; 3) the efficacy of the composition decreased with an increase in the lithium ascorbate proportion and a decrease in the vitamin proportion, as well as with an increase in the vitamin proportion and the decrease in the lithium ascorbate proportion, thus suggesting the synergic effect of the substances used in the composition.

Thus, the use of as a lithium-containing substance in the form of lithium ascorbate as an agent with an anti-stress, anxiolytic and antidepressant effect and a composition based on it allows to expand the assortment of agents for indicated administration. At the same time, the claimed agents have low toxicity and high efficacy.

We claim:

1. A composition useful for treating stress, anxiety or depression in a subject, wherein the following components are present within the composition in the following mass percent ratios: 10-90% lithium ascorbate, 6-50% vitamin B6, and 4-40% vitamin B1.

2. The composition according to claim 1, wherein the composition further comprises cocoa butter.

3. The composition according to claim 1, wherein the composition further comprises at least one additional component selected from the following group consisting of Vitamin A, Vitamin D, Vitamin E, Vitamin K, Vitamin B2, Niacin, Pantothenic acid, Folic acid, Vitamin B12, Biotin, Vitamin C, Calcium, Magnesium, Iron, Copper Iodine, Zinc, Manganese, Sodium, Potassium, Selenium, Chromium, Molybdenum, Fluoride, Chloride, Phosphorus, Levocarnitine, Pantothenic acid (vitamin B5), Choline (vitamin B4), Folic acid (vitamin B9), Glycin (Gly, G), Leucine (Leu, L), Tyrosine (Tyr, Y), Serine (Ser, S), Glutamic acid (Glu, E), Glutamine (Gln, Q), Asparagic acid (Asp, D), Asparagine (Asn, N), Phenylalanine (Phe, F), Alanine (Ala, A), Lysine (Lys, K), Arginine (Arg, R), Histidine (His, H), Cysteine (Cys, C), Valine (Val, V), Proline (Pro, P), Hydroxyprolin (Hyp, hP), Tryptophan (Trp, W), Isoleucine (Ile, I), Methionine (Met, M), Treonine (Thr, T), Hydroxylysine (Hyl, hK), β-Alanine, PQQ (vitamin B14), Astaxanthin, Coenzyme Q10, Succinic acid, Hydroxy-butanedioic acid, Meldonium, Indole-3-carbinol, Rutin.

* * * * *